(12) United States Patent
Allgeyer

(10) Patent No.: US 10,145,784 B2
(45) Date of Patent: *Dec. 4, 2018

(54) INFUSION SET AND SPECTROSCOPIC ANALYZER FOR ANALYSIS OF PHARMACEUTICALS

(71) Applicant: Dean O. Allgeyer, MD, Inc., Los Angeles, CA (US)

(72) Inventor: Dean O. Allgeyer, Los Angeles, CA (US)

( * ) Notice: Subject to any disclaimer, the term of this patent is extended or adjusted under 35 U.S.C. 154(b) by 292 days.

This patent is subject to a terminal disclaimer.

(21) Appl. No.: 14/859,277

(22) Filed: Sep. 19, 2015

(65) Prior Publication Data
US 2016/0011097 A1    Jan. 14, 2016

Related U.S. Application Data

(63) Continuation-in-part of application No. 13/947,772, filed on Jul. 22, 2013.

(51) Int. Cl.
| | |
|---|---|
| *G01N 21/01* | (2006.01) |
| *G01N 21/33* | (2006.01) |
| *A61M 5/14* | (2006.01) |
| *G01N 21/03* | (2006.01) |
| *A61M 5/162* | (2006.01) |
| *G01N 21/11* | (2006.01) |
| *A61M 5/142* | (2006.01) |

(52) U.S. Cl.
CPC ......... *G01N 21/0303* (2013.01); *A61M 5/162* (2013.01); *G01N 21/01* (2013.01); *G01N 21/03* (2013.01); *G01N 21/11* (2013.01); *G01N 21/33* (2013.01); *A61M 5/14* (2013.01); *A61M 5/142* (2013.01); *A61M 2205/02* (2013.01); *A61M 2205/276* (2013.01); *A61M 2205/3313* (2013.01); *A61M 2205/6009* (2013.01); *A61M 2205/6063* (2013.01); *G01N 2201/02* (2013.01)

(58) Field of Classification Search
CPC ......... A61M 3/00; G01N 21/01; G01N 21/07; G01N 21/03; G01N 21/11; G01N 21/33
See application file for complete search history.

(56) References Cited

U.S. PATENT DOCUMENTS

| | | | | |
|---|---|---|---|---|
| 4,038,982 | A * | 8/1977 | Burke ................. | A61M 5/1689 128/DIG. 13 |
| 4,581,014 | A * | 4/1986 | Millerd ............... | A61M 5/1409 604/248 |

(Continued)

*Primary Examiner* — Nicole Ippolito
*Assistant Examiner* — Sean Luck
(74) *Attorney, Agent, or Firm* — Samuel L. Alberstadt

(57) ABSTRACT

An infusion set and an intravenous bag adapter constructed of ultraviolet transmissive thermoplastic are used in spectroscopic validation of pharmaceuticals. The described hardware allows for qualitative and quantitative assurance of medications and is used to prevent medication errors. The thermoplastic is transmissive in the range below 315 nanometers. In one embodiment, the invention comprises a spectrometer and a test chamber that are unaffected by the presence of ambient light. The spectrometer includes an unshielded slot or receptacle into which the test chamber is easily fitted. This embodiment can function well in drug diversion programs for which unused post-op narcotics can be tested.

6 Claims, 3 Drawing Sheets

(56) References Cited

U.S. PATENT DOCUMENTS

| | | | | |
|---|---|---|---|---|
| 5,173,749 A | * | 12/1992 | Tell | G01N 21/031 |
| | | | | 250/343 |
| 5,807,312 A | * | 9/1998 | Dzwonkiewicz | A61M 5/1424 |
| | | | | 604/248 |
| 2003/0045840 A1 | * | 3/2003 | Burko | A61M 5/1689 |
| | | | | 604/253 |
| 2004/0027568 A1 | * | 2/2004 | Maiefski | G01J 3/02 |
| | | | | 356/326 |
| 2008/0051732 A1 | * | 2/2008 | Chen | A61M 5/1689 |
| | | | | 604/253 |
| 2009/0155468 A1 | * | 6/2009 | Petrov | C23C 18/1617 |
| | | | | 427/306 |
| 2009/0157229 A1 | * | 6/2009 | Rulkens | C25D 21/12 |
| | | | | 700/267 |
| 2009/0173145 A1 | * | 7/2009 | Martin | G01N 21/78 |
| | | | | 73/61.41 |
| 2010/0000304 A1 | * | 1/2010 | Kim | B01L 3/5085 |
| | | | | 73/64.56 |
| 2010/0220310 A1 | * | 9/2010 | Blodgett | G01N 21/31 |
| | | | | 356/30 |
| 2010/0277727 A1 | * | 11/2010 | Schlaminger | G01N 21/15 |
| | | | | 356/326 |
| 2010/0324505 A1 | * | 12/2010 | Levenson | A61M 25/0097 |
| | | | | 604/247 |

* cited by examiner

INFUSION SET AND SPECTROSCOPIC ANALYZER FOR ANALYSIS OF PHARMACEUTICALS

APPLICATION HISTORY

This application is a continuation-in-part (CIP) of, and claims the benefit of the filing date of, application Ser. No. 13/947,772, filed Jul. 22, 2013, Publication No. 2015/0021494, published Jan. 22, 2015.

FIELD OF THE INVENTION

This invention relates to the spectroscopic analysis of chemical compounds. More specifically, one form of the invention relates to an adapter and an infusion set for use in verifying pharmaceuticals as a means to prevent medication errors. This form of the invention includes a chamber that is substantially transmissive of ultraviolet radiation that is unaffected by ambient light in a clinical setting, even with a spectroscopic reader that functions in an unshielded configuration. Another form of the invention is a system that includes a spectroscopic analyzer with an unshielded receptacle for a cuvette, in which the cuvette is substantially transmissive of ultraviolet radiation such that the system is unaffected by ambient light in a clinical setting.

BACKGROUND OF THE INVENTION

The problem of medication errors has been well documented. In U.S. Pat. No. 6,847,899 to Allgeyer, incorporated herein by reference in its entirety, Allgeyer discusses these issues. In 2012, a Becton-Dickinson study addressed quantification of the problem: Preventable Adverse Drug Events (ADEs) associated with injectable medications impact more than 1 million hospitalizations each year, and they increase annual costs to U.S. healthcare payers by $2.7 billion to $5.1 billion. Those costs represent an average of $600,000 per hospital each year. The medical professional liability cost for inpatient ADEs from injectable medication reaches an industry-wide $300 million to $610 million annually, or as much as $72,000 per hospital. Preventable ADEs are associated with a large range of harmful pharmaceuticals, from heparin to morphine. For example, a common error resulting in fatalities and severe injuries is the so-called 10× error, in which the mistake of a single decimal place occurs in compounding or in programming an infusion pump. In 2007, the well-publicized injection of 1,000 times the intended heparin dose to the newborn twins of celebrity Dennis Quaid highlighted the continuing and long-felt need to control ADEs in clinical settings.

Given the magnitude and seriousness of the ADE problem, there are many ongoing strategies to address and mitigate the risks. Becton-Dickinson utilizes a vibrational spectroscopic technique, wherein the sensor is in contact with the fluid to be analyzed. See US 2012/0226446; US 2012/0226447; and, US 2012/0226448. Approaches utilizing fluorescence, NIR, Raman analysis, and other methods have been developed. These ostensible improvements have turned out to be unsatisfactory, because they are ineffective when used in ambient light, thus requiring some sort of shielding. See, e.g., US 2004/0027568 to Maiefski et al, and US 2009/0157229 to Rulkens et al, both cited during prosecution of the parent application. To date, excluding ambient light has added complexity and costs to workflow and hardware requirements. As yet, however, no system of medication verification has adequately combined the features of reliability, accuracy, low cost, simplicity, and ease of use, especially in a clinical context where ambient light is unavoidable.

SUMMARY OF THE INVENTION

It is, therefore, an object of the present invention to provide an intravenous bag adapter or an infusion set that can be utilized reliably, accurately, and with a minimum of cost and complexity. Similarly, the invention provides a spectroscopic analyzer—also known as a spectrometer, spectrophotometer, or spectrograph—and a container (such as a cuvette) that are easy to use together. A singular feature of the invention is that it can be used in a clinical context without shielding from ambient light. In particular, the chamber of the adapter and infusion set is transmissive of ultraviolet (UV) wavelengths. Utilizing spectroscopy with a quartz cuvette and wavelengths below 315 nanometers (nm) yields accurate qualitative and quantitative results for the high-risk pharmaceuticals responsible for the majority of adverse drug events and deaths. Quartz cuvettes, however, can be impractical for this application due to their fragility, rigidity, and cost. Polycyclic polyolefin has roughly 82 percent transmission at 280 nm, compared to 90 percent for quartz. Based on the Beer-Lambert law, dimensional tolerances can be relatively liberal while providing meaningful information regarding drug concentration in the context of common dosage errors. Therefore, a significantly UV transmissive moldable thermoplastic, an IV bag adapter or infusion set, or an unshielded cuvette usable in ambient light with an unshielded spectrometer, result in a system for reliable and inexpensive pharmaceutical verification. By using the moldable thermoplastic, the components can be disposable.

In order to facilitate and improve medication verification—especially prior to use—it is highly desirable to integrate a new process into existing workflow patterns. Currently, any compounded IV bag requires that an infusion set be "spiked" or attached to the bag prior to infusion. By adapting an infusion set for pharmaceutical verification, the existing workflow is unchanged except for the step of inserting the adapter or infusion set into the spectrophotometric reader. With the present invention, this step can be performed in real time in the pharmacy, in the patient care area such as a nursing station, or at the point of care. Similarly, an IV bag adapter can be spiked in the pharmacy for verification, a label then attached, and the bag sent to where it can be spiked with a conventional infusion set.

UV absorption spectroscopy below 315 nm is accurate with an unshielded sample. This result occurs because incandescent and fluorescent light emits no energy below this wavelength while sunlight emissions below 315 nm are filtered by atmospheric ozone. Therefore, ambient light such as that found in a pharmacy or patient ward, whether artificial or from an adjacent window, has no effect on pharmaceutical analysis utilizing wavelengths below 315 nm and allows for verification in these environments. Therefore, it is desirable to have an IV adapter or IV infusion set that can be used with a spectrometer in wavelengths less than 315 nm.

Limiting the fluid testing to the UV range in an unshielded spectrometer also allows for arrangements unique to medical applications and dramatically simplifies workflow. For example, FIG. 4 of the present application depicts an IV set that is primed with IV medication and is being analyzed for quality assurance prior to administration to the patient. A shielded chamber would preclude the use of this arrangement, due to the length of a standard IV set of approximately seven feet. It would require a sample from the bag or from the end of the IV set of a small aliquot of fluid. Both are unacceptable. In the first instance sterility is compromised and in both instances the operator is potentially exposed to the fluid. Chemotherapeutic agents in IV form are one of the significant applications of the invention, so operator exposure is unacceptable for reasons of occupational health.

Furthermore, the current invention functions well with pharmaceutical specimens for which sterility need not be maintained and which are not considered an aerosolized or contact risk. In other words, for those situations a sample can be obtained from a source and placed in an open container such as a cuvette. This can be accomplished in several ways, such as piercing a used IV bag with a syringe, withdrawing the pharmaceutical, and placing it in the claimed testing chamber, which could take the form of a cuvette.

In one embodiment, the present invention comprises an IV bag adapter that includes a test chamber that is substantially transmissive of ultraviolet radiation below about 315 mm. In another embodiment, the invention comprises an infusion set that includes a test chamber that is substantially transmissive of ultraviolet radiation below about 315 nm. In yet another embodiment the invention includes a spectrometer that is insubstantially shielded from ambient light and a chamber, such as a cuvette, which receives a pharmaceutical fluid that is tested in the spectrometer. In addition, the cuvette, or test chamber, can be placed directly into the spectrometer, an improvement over the prior art. Such a configuration can be used in a drug diversion program that analyzes a small percentage of returned, unused narcotics from an operating room. Such a program could detect and deter medical personnel who divert narcotics principally for self-administration. Moreover, it permits an organization such as a hospital to pursue the program in-house. This is a far less expensive approach than collecting scores of postoperative samples and sending them out to a laboratory to have them tested.

DETAILED DESCRIPTION OF THE PREFERRED EMBODIMENTS

The present invention is an IV bag adapter or infusion set with a test chamber that is substantially transmissive of UV light in a range that is not affected by ambient lighting in a clinical setting. Both the adapter and the infusion set are designed to be inexpensive and disposable and molded within a tolerance that gives meaningful quantitative data regarding drug concentrations.

Figure 1:
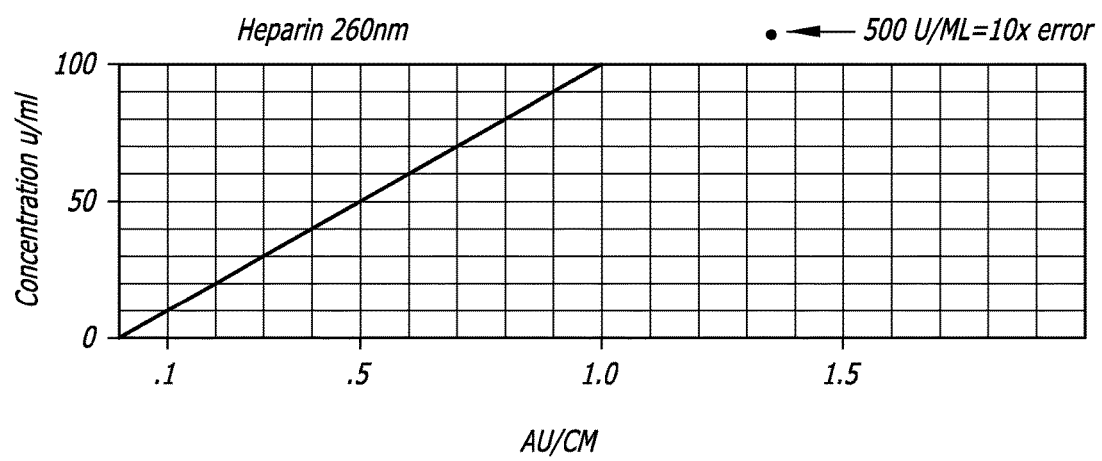
FIG. 1 illustrates a linear calibration curve for Heparin 50 u/cc at 260 nm.

As an example of one injectable medication, FIG. 1 illustrates a Heparin calibration plot at 260 nm. Concentration in units/ml (U/ml) is plotted against absorption units (AU) per centimeter (AU/cm). The plot is stored in the memory of a spectrometer (See FIG. 4) for automated comparison of a recently compounded preparation. An acceptable variance can be programmed into the spectrometer, which in the case of heparin is a realistic level on the order of ±25 percent. Widely divergent samples that represent potential ADE's are readily identified due to the magnitude of the discrepancies, preventing harm to patients. FIG. 1 shows a 50 u/cc concentration with an AU/cm value of 0.5. A 10-fold error plots a reading of 1.35 AU/cm. Therefore, the frequently encountered 10× error would easily be recognized, and the heparin sample would be rejected when tested. With such testing accuracy, the 1,000× heparin error suffered by the Quaid twins would never recur.

Figure 2:
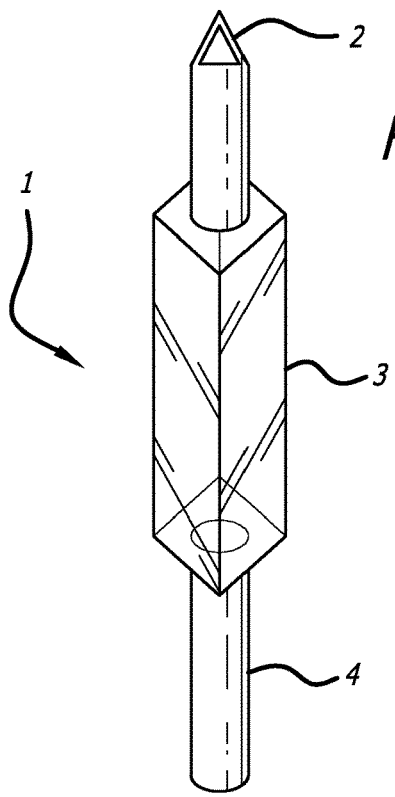
FIG. 2 illustrates an IV bag adapter.

FIG. 2 illustrates an adapter 1 for an IV bag (not shown). Typically, a medication for IV infusion will be stored (or individually compounded) in a plastic bag in the pharmacy of a hospital. When a physician orders the medication for a patient, the pharmacy retrieves it from storage, or compounds it if necessary, and sends it to the patient's floor and nursing station for infusion. After an IV bag is compounded and before being sent to the floor, IV bag adapter 1 is sterilely inserted via spike 2 into the receptacle of the IV bag, which is of the same dimensions of receptacle 4. Adapter test chamber 3 is purged of air and filled by IV fluid bag contents by repetitive squeezing of the IV bag and chamber 3 until the chamber is preferably at least half full. This maneuver, besides preparing the solution for spectroscopic testing, has the additional salutary effect of ensuring the mixing of the IV bag's contents. The adapter 1 is then inserted into receptacle or slot 12 of spectroscopy enabled reader 7, FIG. 4 discussed below, and the fluid is verified as to drug contents and concentration by comparing it to a previously entered physician's order. That the test chamber is filled at least half way enables the UV waves to pass through the solution as opposed to air. In other words, reader 7 in FIG. 4 has a "light path" in the lower half of slot 12. If the fluid is verified, a bar coded label is printed and affixed to IV bag which contains pertinent information including patient name, drug and concentration, time of admixture, physicians name, etc. In this way, compounding and mislabeling errors are curtailed. Spike 2 and receptacle 4 can be supplied with a peal-off plastic covering (not shown), which ensures sterility until testing.

Figure 3:
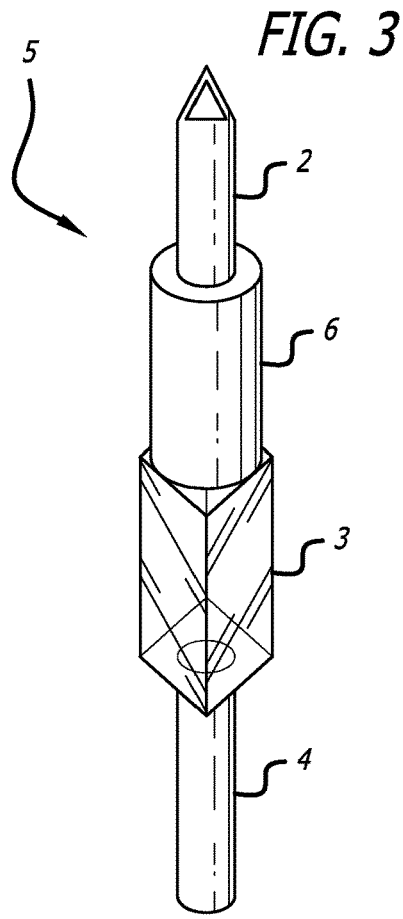
FIG. 3 illustrates the IV infusion set, including drip chamber but without the tubing that usually comes with an infusion set.

FIG. 3 illustrates drip chamber 6 of an infusion set 5 that sits atop test chamber 3, which is also constructed of substantially UV-transmissive material. While conventional thermoplastics—like polyethylene, polystyrene, and polyurethane—have proven substantially UV-transmissive, polycyclic polyolefin has proven to be an ideal material when all factors are considered. Infusion set 5 can be used in lieu of IV bag adapter 2, as is often the case in clinical practice. In this instance, infusion set 5 with chamber 3 can be placed into the receptacle of a spectroscopically enabled reader (see FIG. 4) for verification of drug type and concentration. This could take place on the patient ward if the hospital so chooses, such that in pharmacy verification is omitted. It is noted that adapter or test chamber 3 of both the IV bag adapter 1 and IV infusion set 5 are preferably of the same dimension and the spectroscopically enabled reader is constructed to interact and function with either device such that a reader of a single design and dimensions can be utilized.

Figure 4:
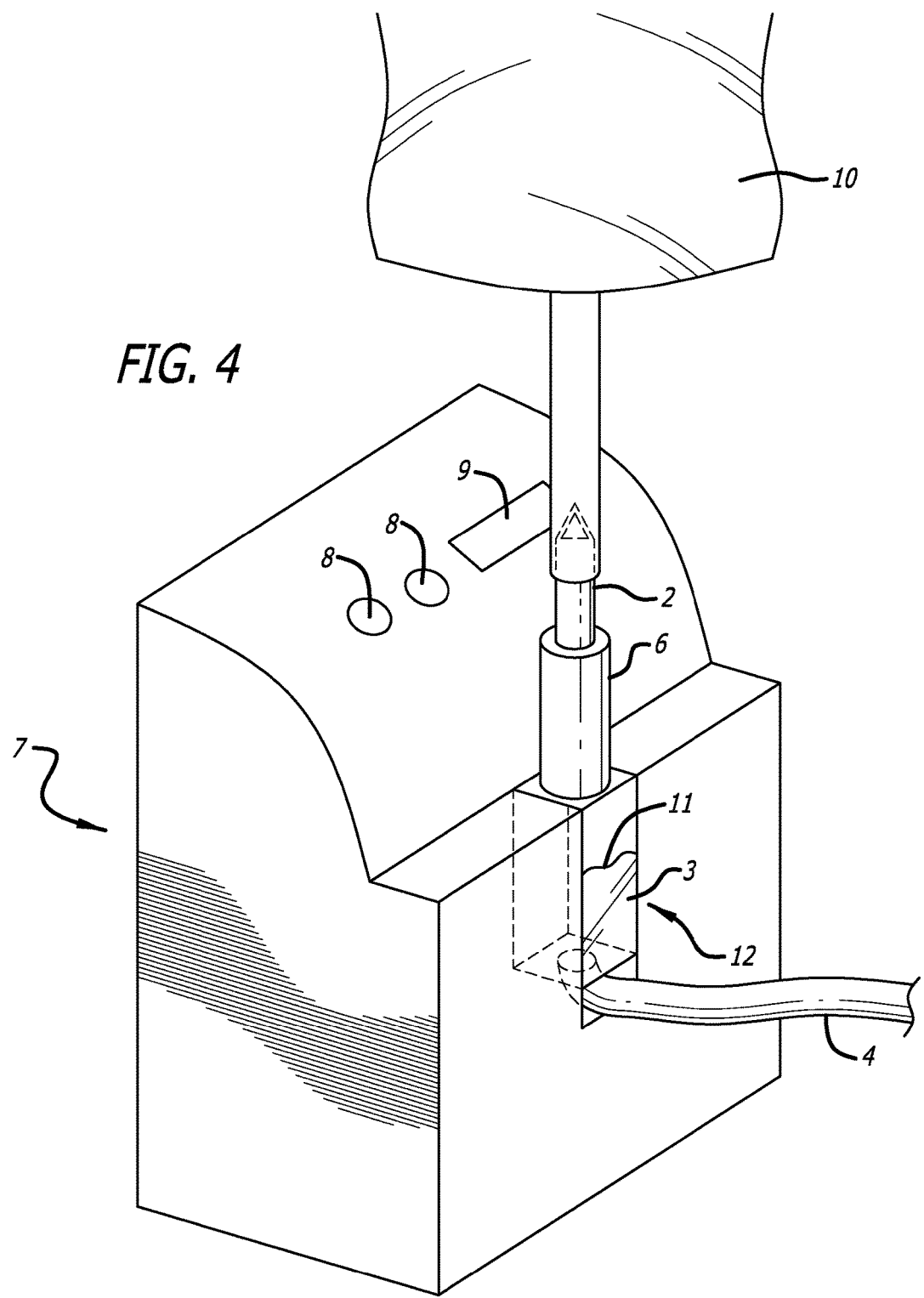
FIG. 4 illustrates a device with a UV transmissive chamber being inserted into a spectrometer.

FIG. 4 represents a generic spectroscopic analyzer or spectrometer 7 for reading the fluid contents of test chamber 3. Once chamber 3 has been filled to a minimum level 11 of at least one half from IV bag 10, the IV bag adapter 2 or infusion set 5 can be inserted into receptacle or slot 12 of analyzer 7. Controls 8 are utilized to control analysis that is monitored on screen 9. The various types of controls will be known by those of skill in the art, and may include dials, buttons, keyboards, touch screens, and the like, that are part of or operatively connected to the spectrometer. Analyzer 7 can be networked with a computerized physician order entry system, and once verification has occurred, a bar coded label (not shown) can be printed and affixed to IV bag 10, which is then distributed to the point of care. Depending on the preference of the institution, the invention and a verification system can be configured be in numerous ways to decrease medication errors. For example: A hospital may want to batch-compound a morphine solution to be used for filling multiple IV bags for use with patient controlled anesthesia pumps. After a hundred bags are filled from the morphine stock preparation, a number of bags may be randomly chosen for analysis and verification utilizing IV adapter 1. If the verification is consistent with the purported drug and its specified concentration, those bags can be labeled and sent to the patient care areas for use. In this way the drug and concentration is verified and the hospital can save money by batch-compounding high-risk drugs with assurance. Once ready for infusion at the bedside, the barcode may be read by the barcode-enabled infusion pump, which also contains an institutional reference of normal values based on patient weight, age, etc. Should the pre-established institutional norms be exceeded, an alert would be displayed and the infusion pump would immediately be locked or stopped to prevent administration of the incorrect medication. In this manner, errors of compounding or pump programming are discovered and prevented. Institutions could deploy other strategies for prevention of medication errors and or diversion of medications. For example, infusion set 5 can be used at the point of care in a continual surveillance mode. Drip chamber 6 of IV infusion set 5 can be monitored spectroscopically in such a fashion by placing it into the receptacle with a spectroscopically enabled sensor. It can then be clamped to the drip chamber or pole mounted and then connected to the infusion pump for real time monitoring of drug infusion.

Figure 3A:
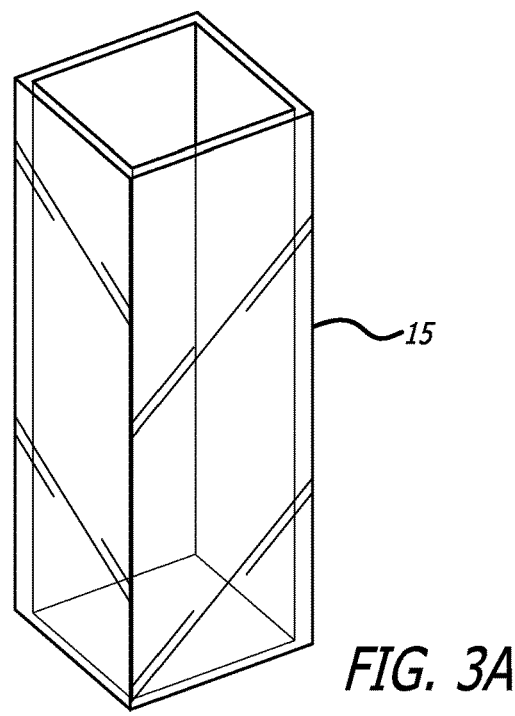
FIG. 3A illustrates a cuvette that can be used with the spectrometer depicted in FIG. 4.

The embodiment in FIG. 4 can be modified so that the invention may be used in other ways. For example, infusion set 5 can be eliminated from the figure, leaving just test chamber 3 sitting in slot or receptacle 12 of analyzer 7. Test chamber 3 can be a quartz or plastic cuvette, such as cuvette 15 depicted in FIG. 3A. The cuvette is designed to provide a light path across which the spectrometer or analyzer 7 performs its analysis. This arrangement provides an easily accessible spectrometer and test chamber that is not designed to shield the sample in the test chamber from ambient light. In other words, it allows the test chamber 3 to be placed directly in the receptacle 12 without other significant manipulations of the spectrometer. This configuration distinguishes the invention from prior art such as Maiefski, which requires substantially more effort to place a test sample in the spectrometer. Depending on the nature of the pharmaceutical to be tested, it may or may not be desirable for the test chamber to have some type of cap to seal the pharmaceutical in the chamber. Thus, potentially toxic or harmful pharmaceuticals, such as anti-cancer drugs, can be contained and prevented from spilling on the individual performing the testing.

As those of skill in the art will appreciate, the combination of the unshielded analyzer and test chamber is not limited to the spectroscopic analyzer depicted in FIG. 4. An important feature of the invention is the easy and unshielded accessibility of spectrometer's receptacle, so that the test chamber can be placed and tested in with minimal time and difficulty. When a substantial number of tests of the same fluid are performed, this process can dramatically reduce the cost of testing. Whether a test chamber is rectangular, square, round, or any other shape, and whether the receptacle can accommodate more than one type of test chamber, are matters for the designer. Consistency and repeatability are necessary for the invention to work properly. Similarly, the nature of the spectrometer and the controls is a matter of choice for the designer. More and more, controls and information displays are being integrated into a single touch-screen, with the functions being hardwired inside the device. It will be apparent to those skilled in the art that modifications, variations, and equivalents of the invention can be made without departing from the scope of the invention as detailed in the claims below.

What is claimed is:

1. A system for spectroscopically analyzing a pharmaceutical fluid, comprising:
   a spectrometer;
   a test chamber in the spectrometer for receiving the pharmaceutical fluid, the test chamber also comprising a translucent material that is transmissive of ultraviolet light; and,
   wherein the test chamber and spectrometer are configured to provide a fixed, substantially unshielded path for ultraviolet light to be used in the quantitative application of Beers law to the pharmaceutical fluid and wherein the test chamber is substantially unshielded from ambient light.

2. The invention of claim 1, wherein the testing chamber is transmissive of ultraviolet light having a wavelength equal to or less than 315 nanometers.

3. The invention of claim 2, wherein the testing chamber is comprised of a thermoplastic.

4. The invention of claim 3, wherein the thermoplastic is a polycyclic polyolefin.

5. The invention of claim 1, wherein the testing chamber is transmissive of ultraviolet light having a wavelength equal to or less than 315 nanometers and is comprised of a thermoplastic.

6. The invention of claim 1, further comprising a receptacle for receiving and holding the chamber during testing, and also adapted so that during testing the chamber in the receptacle is substantially unshielded from ambient light.

* * * * *